United States Patent
Horwitz

(10) Patent No.: US 8,992,586 B2
(45) Date of Patent: Mar. 31, 2015

(54) MINIMAL INCISION REMOVABLE BONE SCREW, DRIVER, AND METHOD OF USE

(71) Applicant: Michael H. Horwitz, St. Louis, MO (US)

(72) Inventor: Michael H. Horwitz, St. Louis, MO (US)

(*) Notice: Subject to any disclaimer, the term of this patent is extended or adjusted under 35 U.S.C. 154(b) by 44 days.

(21) Appl. No.: 14/054,344

(22) Filed: Oct. 15, 2013

(65) Prior Publication Data
US 2014/0046384 A1 Feb. 13, 2014

Related U.S. Application Data

(63) Continuation of application No. PCT/US2012/047743, filed on Jul. 20, 2012.

(60) Provisional application No. 61/673,681, filed on Jul. 19, 2012, provisional application No. 61/509,940, filed on Jul. 20, 2011.

(51) Int. Cl.
*A61B 17/86* (2006.01)
*A61B 17/88* (2006.01)

(52) U.S. Cl.
CPC ....... *A61B 17/863* (2013.01); *A61B 2017/8655* (2013.01); *A61B 17/8883* (2013.01); *A61B 17/862* (2013.01); *A61B 17/8625* (2013.01); *A61B 17/864* (2013.01); *A61B 17/8875* (2013.01)
USPC ........................................................ 606/304

(58) Field of Classification Search
CPC ............. A61B 17/862; A61B 17/8625; A61B 17/863; A61B 17/864; A61B 2017/8655
USPC ......... 606/300, 301, 307, 309, 310, 313, 319, 606/320, 326–328; 411/402, 424, 426
See application file for complete search history.

(56) References Cited

U.S. PATENT DOCUMENTS 519,962 A * 5/1894 Mallock .......................... 81/450
1,331,824 A * 2/1920 Powers ........................... 81/462
(Continued)

FOREIGN PATENT DOCUMENTS

WO 2013013218 A2 1/2013

OTHER PUBLICATIONS

International Search Report for PCT application PCT/US2012/047743 mailed Feb. 21, 2013.
(Continued)

*Primary Examiner* — Michael T Schaper
(74) *Attorney, Agent, or Firm* — Polster, Lieder, Woodruff & Lucchesi, L.C.

(57) ABSTRACT

A surgical bone screw (1) and driver (31), and a method for using them for repairing an osteotomy or fracture. The screw has a shaft having a head (5) at its proximal end, screw threads (3) at its distal end and a compression member (7) between the head and the screw threads. In an embodiment, the threads are self-tapping and self-drilling, the head is polygonal, and the sides of the polygon are convex. The driver turns the screw until the threads cross a fracture site and the compression member contacts the proximal bone fragment. The threads and compression member draw the fragments together and leaves the head entirely clear of the bone surface. The screw is removed through a small incision. Tilting the driver to allow the socket to engage an inwardly extending lower portion of the head permits the driver to lift the screw out of the bone.

12 Claims, 9 Drawing Sheets

(56) References Cited

U.S. PATENT DOCUMENTS

| | | | | |
|---|---|---|---|---|
| 1,398,234 A * | 11/1921 | Landis | | 81/450 |
| 1,628,553 A * | 5/1927 | Owens | | 81/436 |
| 2,008,229 A | 7/1935 | Sharp | | |
| 2,016,610 A | 10/1935 | Moeller | | |
| 2,024,071 A | 12/1935 | Taylor et al. | | |
| 2,229,565 A * | 1/1941 | Hallowell, Jr. | | 411/403 |
| 2,679,778 A * | 6/1954 | Krafft | | 81/439 |
| 3,604,486 A * | 9/1971 | Henry | | 81/450 |
| 3,769,665 A * | 11/1973 | McKown, Jr. | | 24/274 R |
| 4,028,968 A * | 6/1977 | DeAmicis | | 81/450 |
| 4,246,811 A * | 1/1981 | Bondhus et al. | | 81/436 |
| 4,711,232 A | 12/1987 | Fischer et al. | | |
| 4,808,051 A | 2/1989 | Gietl | | |
| 4,854,311 A | 8/1989 | Steffee | | |
| 5,019,078 A * | 5/1991 | Perren et al. | | 606/313 |
| 5,019,080 A | 5/1991 | Hemer | | |
| 5,251,521 A * | 10/1993 | Burda et al. | | 81/460 |
| 5,336,225 A | 8/1994 | Zang | | |
| 5,375,956 A | 12/1994 | Pennig | | |
| 5,421,684 A * | 6/1995 | Kluemper | | 411/392 |
| 5,540,690 A * | 7/1996 | Miller et al. | | 606/287 |
| 5,545,163 A | 8/1996 | Miller et al. | | |
| 5,606,898 A * | 3/1997 | Franciskovich et al. | | 81/436 |
| 5,682,651 A * | 11/1997 | Sauer | | 24/274 R |
| 5,682,801 A * | 11/1997 | Waechter | | 81/121.1 |
| 5,779,704 A * | 7/1998 | Kim | | 606/64 |
| 5,968,047 A | 10/1999 | Reed | | |
| 6,016,727 A | 1/2000 | Morgan | | |
| 6,158,094 A * | 12/2000 | Clanin | | 24/274 R |
| D461,544 S * | 8/2002 | Crockett, IV | | D23/265 |
| 6,766,993 B2 * | 7/2004 | Rasmussen et al. | | 248/313 |
| 6,916,321 B2 | 7/2005 | TenHuisen et al. | | |
| 7,044,953 B2 | 5/2006 | Capanni | | |
| 7,090,680 B2 | 8/2006 | Bonati et al. | | |
| 7,582,093 B2 | 9/2009 | Vasta et al. | | |
| 7,615,069 B2 | 11/2009 | Paul | | |
| 7,727,235 B2 | 6/2010 | Contiliano et al. | | |
| 8,221,478 B2 | 7/2012 | Patterson et al. | | |
| 2001/0053913 A1* | 12/2001 | Freedland | | 606/73 |
| 2004/0116932 A1* | 6/2004 | Mazda et al. | | 606/73 |
| 2006/0069393 A1 | 3/2006 | Pathak | | |
| 2006/0276792 A1* | 12/2006 | Ensign et al. | | 606/61 |
| 2007/0270880 A1 | 11/2007 | Lindemann et al. | | |
| 2011/0190821 A1* | 8/2011 | Chin et al. | | 606/264 |
| 2013/0030474 A1* | 1/2013 | Chaput | | 606/305 |

OTHER PUBLICATIONS

Written Opinion of the International Search Authority for PCT application PCT/US2012/047743 mailed Feb. 21, 2013.

* cited by examiner

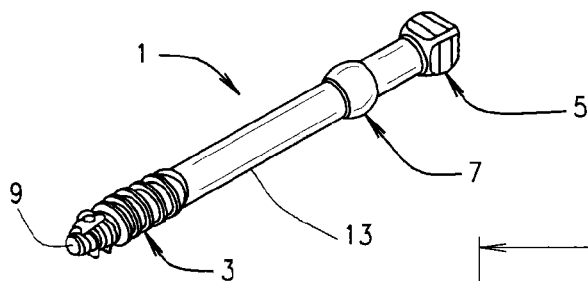
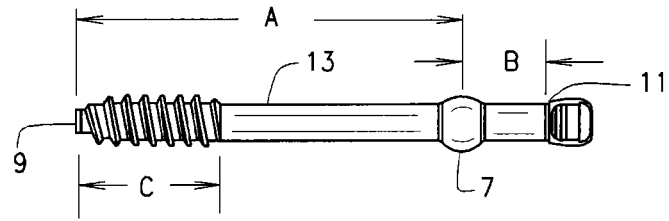
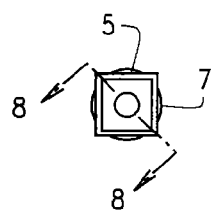
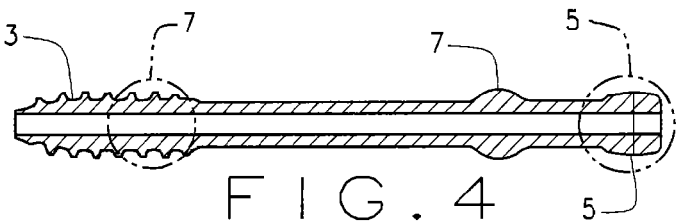
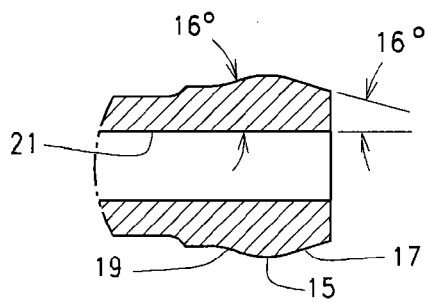
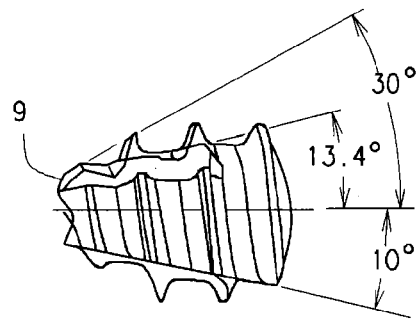
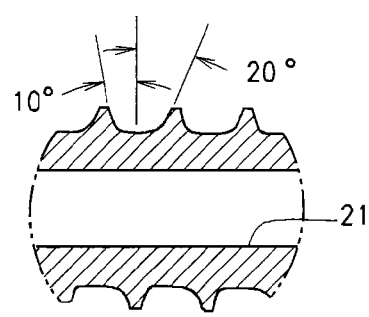
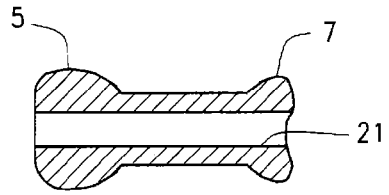

MINIMAL INCISION REMOVABLE BONE SCREW, DRIVER, AND METHOD OF USE

CROSS-REFERENCE TO RELATED APPLICATIONS

This application is a continuation of International Application No. PCT/US2012/047743, filed Jul. 20, 2012, which is related to, and claims priority from U.S. provisional applications Ser. No. 61/509,940, filed 20 Jul. 2011, and Ser. No. 61/673,681 filed 19 Jul. 2012, the disclosures of which are hereby incorporated by reference.

STATEMENT REGARDING FEDERALLY SPONSORED RESEARCH

Not Applicable.

TECHNICAL FIELD

The present invention relates to a bone screw, a driver for the screw, and a method of applying and removing the screw. The system may be used as a removable fixation system for any osteotomy or fracture requiring lag compression. The screw has particular application for interfragmentary internal fixation of small bones, such as those of the foot, hand, and ankle, but is also useful with osteotomies or fractures of large bones and spine.

BACKGROUND ART

When a bone is fractured, either by deliberately cutting it (osteotomy) or by trauma, it heals better if the bone fragments are pressed firmly together. Compression of the fragments increases the contact area across the fracture and increases stability of the bone at the fracture. It also decreases stress on any orthopedic implant.

Internal fixation of a bone fracture using bone screws is now common practice. The screw is applied across the fracture, preferably at nearly a right angle to the fracture, although the nature of the bone and of the fracture frequently dictates other angles. The distal end of the screw crosses the fracture, and when the head of the bone screw engages the proximal fragment, further rotation of the screw draws the distal fragment of the bone against the proximal fragment. Any screw that is used to achieve interfragmental compression is termed a lag screw. The two most common types of lag screws are cortical and cancellous screws. Cortical screws have fine threads on their shaft and are designed to anchor in cortical bone. Cancellous screws tend to have coarser threads and are designed to anchor in the softer cancellous bone.

Both types of lag screw generally include a threaded distal end and a proximal head. Although the screw may be threaded nearly to the head, this design requires that the proximal bone fragment be pre-bored to permit the threads to pass smoothly through the proximal fragment. More commonly, the threads on the distal end extend only far enough to ensure a positive grip in the distal fragment but not so far as to engage the proximal fragment when the screw is applied, the shaft between the threads and the head being smooth and sized no larger than the minor diameter of the threads (the maximum diameter of the thread groove). The distal side of the head, facing the shaft, is usually symmetrically convex, preferably hemispherical, and the proximal face of the proximal bone fragment is frequently lightly countersunk, in order to spread stresses in the screw and the bone most efficiently, to reduce the risk of creating a stress fracture, and to minimize the protrusion of the screw head from the face of the bone. The upper, proximal, side of the screw head is generally flat or gently rounded to permit the head to lie as close to level with the proximal bone surface as possible. The head is provided with a slot, spaced holes, a hexagonal socket, or other depression to accept the blade or tip of a drive tool or screwdriver designed to be inserted into it.

In order to eliminate the need for pre-drilling bone and tapping the distal bone fragment, bone screws are now frequently made to be self-tapping. To aid further in the placement of bone screws, the screws are frequently cannulated, having a hollow shaft and head. Cannulated screws may be placed more precisely than non-cannulated screws. The surgeon first drills a small Kirschner wire (K-wire) across the fracture, generally under fluoroscopic control. The wire may sometimes be inserted through the skin without the need of an incision. If necessary, the K-wire can be withdrawn and replaced with minimal trauma to the bone in order to place it in optimal position across the fracture. A small incision may then be made through the skin to enable the surgeon to minimize tissue trauma while placing the bone screw and to permit countersinking the bone around the point of insertion of the screw. The cannulated screw is then placed over the wire and slid down to the bone surface. A special cannulated driving tool then allows the screw to be driven into the bone along the shaft of the K-wire. The K-wire is then withdrawn and the wound over the screw is closed.

The construction and use of bone screws has become standardized to a great extent. There are of course, many variations on the details of the construction of bone screws, including for example, the use of a break-away driven element as shown in Patterson et al, U.S. Pat. No. 8,221,478.

Bone screws may also be designed merely as an anchor for attaching an external stabilizing device. Pedicle screws, such as illustrated in Mazda et al., U.S. published application US 2004/0116932 A1, are examples of such external fixation screws. The present invention is not principally concerned with such screws, although some aspects of the invention may be applicable to them.

Internal fixation bone screws may be left in the body after implantation. However, surgeons are increasingly removing fixation for a number of justifiable reasons. Irritation/inflammation, allergic reaction, and infection are common reasons to remove hardware at appropriate times. Although rare, implant rejection may occur. Furthermore, the long-term deleterious effects of a metal such as stainless steel or a titanium alloy implanted in the body are not fully understood. It is not uncommon for barometric pressure and changes in ambient temperature to cause rheumatic or osteoarthritic flare-ups. The possibility of a causal relationship influenced by hardware left in and around these areas exists. Finally, because of growing concerns over electro-magnetic radiation caused by cell phone use and other exposure, it is ideal that conductive metals be removed from the body if possible. MRI and other present electromagnetic technologies are influenced by conductive, metallic implants. Future technologies may depend on the body being free of conductive elements. Therefore, particularly when a deleterious effect is noted, a bone screw is sometimes removed, thereby allowing bone regeneration in the volume formerly occupied by the bone screw. Such removal, however, requires considerable effort and risk, as suggested by patents such as Bonati et al., U.S. Pat. No. 7,090,680, Steffee, U.S. Pat. No. 4,854,311, Vasta et al., U.S. Pat. No. 7,582,093, or Lindemann et al., U.S. published application US 2007/0270880 A1. Special screw removal kits including multiple instruments are commercially available.

When faced with having to remove a screw of the prior art, a surgeon must deal with creeping fibrosis, meaning soft tissues that creep into the screw threads making it difficult to access the screw without an incision into periosteal structures and more trauma. Fibrosis, in a worst-case scenario will make it necessary for a full screw extraction set to be utilized thereby completely bypassing the conventional methodologies of placing a screwdriver into a head. This usually requires cutting the screw or severe countersinking.

In order to overcome these problems, some bone screws are made of absorbable materials. These screws, however, are not as strong as metal screws, require drilling and tapping with metal instruments, and are transparent to x-rays. Hybrid metal and polymer screws are disclosed in Fischer et al., U.S. Pat. No. 4,711,232 and in TenHuisen et al., U.S. Pat. No. 6,916,321, but these screws add complexity and do not solve all of the problems with leaving metal in the body. Another solution has been the use of screws made of compatible bone, as in Reed, U.S. Pat. No. 5,968,047. This approach is costly and has not been entirely satisfactory.

BRIEF SUMMARY OF THE INVENTION

Briefly stated, the present invention provides a bone screw which is easily placed and easily removed, usually after bone healing. The bone screw may be placed and removed using a simple screwdriver in accordance with the invention.

In accordance with one embodiment, a bone screw comprises a thread at its distal end, a head at its proximal end, and a bone-engaging compression member spaced distally from the head. The screw may be made of any biocompatible material, but is preferably made of stainless steel, titanium, or titanium alloy.

Preferably, the thread does not extend as far as the compression member. Preferably, the thread is self-tapping. In some situations it may be self-drilling, although this is not presently preferred. A thread which is neither self-tapping nor self-drilling is also useable. Many types of threads are known and are useable. Both cortical and cancellous screw threads may be used. If the threads extend to or nearly to the compression member, the proximal bone fragment must be pre-drilled to a diameter as great as the thread major diameter to allow the compression member to create a lag effect on the fracture. The depth and shape of the threads, and their length may be established in accordance with known parameters.

Preferably, the bone-engaging compression member is convex on its distal side and is circular in cross-section. Preferably the compression member is convex on its proximal side and has a smoothly curved outline without edges to permit easy extraction through an incision and to provide a neck between the head and the compression member. A ball having a diameter from 10% to 70% greater than the screw diameter is preferred. A ball diameter of 110% to 140% of the maximum major thread diameter or a diameter of 125% to 160% of the shaft diameter is particularly suitable.

The head is preferably non-circular as viewed in top plan elevation (end-on), so that its periphery may be drivingly engaged by a driver. Also preferably, at least two opposed sides of the head are curved inward toward both the proximal end of the screw and the distal end of the screw to enable a hollow head of a screw driver to engage the screw head to transmit sufficient torque to drive screw into or out of bone when the driver is tilted at angles of up to fifteen degrees or possibly twenty degrees from the axis of the screw (+/−15°- 20° articulation). The inwardly curved distal faces of the head also permit the screw to be drawn out of the bone and incision when the driver is articulated away from the axis of the screw.

In a preferred embodiment, the head is in end view a regular polygon having an even number of sides, preferably four or six. With the polygonal configuration, it is convenient for the distance between opposite sides to be about equal to the major thread diameter, ±5%. Thus, for example, a two millimeter screw (having a major thread diameter of two millimeters) may have a two millimeter square head, and a five millimeter screw may have a five millimeter square head. The height of the head, in accordance with the geometry of its sides, is generally about the same as its width, typically on the order of 80% to 100% of its width, usually 90% to 95% of the major thread diameter.

The spacing distance between the base of the head and the widest part of the compression member may be chosen to suit the use of the screw. For some applications, the head is placed just below the skin, without causing the skin to "tent", so it can be found easily by subcutaneous palpation and removed easily with minimal trauma to surrounding tissue. For these applications, a screw having a spacing distance of about three to nine millimeters may be used. Because the screw will generally be removed in a few weeks, accessibility of the screw for ease of removal dictates that in many situations a screw having a long spacing be placed so that the head extends into a concavity below the surface of the epidermis. For other applications, patient comfort or anatomy demands a head that is closer to the bone surface. For these applications a spacing distance of one to three millimeters may be used, and if the screw cannot be found by palpation, it may be found by mechanical or machine means, such as by fluoroscopy.

In most instances, the axial distance from the top (proximal end) of the head to the widest part of the compression member is greater than the largest diameter of the head.

In preferred embodiments, the head and compression member are formed with no sharp edges. All edges are rounded as much as is consistent with maintaining a non-circular head which may be driven by a socket extending over the head and engaging its periphery, so as to maintain the lowest practical coefficient of friction (interaction) between the screw and surrounding soft tissue including nerves and blood vessels after the driver is removed. The top (proximal end) of the head may be flat to minimize height above the working sides of the head, or it may be convex, even spherical, to minimize friction with surrounding tissue and nerves (neuropraxia).

The screw may be either solid or cannulated. When cannulated, the size of the cannula may be chosen in accordance with the size of the wire or pin. K-wire sizes from about 0.7 mm to about 1.6 mm are common. Illustrative screws of the present invention have cannulae which typically range from about 0.75 mm for a two millimeter diameter screw to about 1.4 mm for a seven millimeter diameter screw.

A set of screws of the present invention may include several families of screws of different diameters, for example 2.0, 2.5, 3.0, 3.5, 4.0, 5.0, 6.0, and 7.0 mm. Each family may include screws of different lengths, measured from the distal end of the screw to the maximum diameter of the compression member, ranging, say, from 8 mm to 60 mm in two millimeter increments. Each length of each family may in turn include different compression member-to-head base dimensions, say 1.0 mm, 3.5 mm, 5.0 mm, and 8.0 mm. Because the size of the screw head in each family is constant, the overall length of the screws of a given nominal length may vary based on the length of the compression member to head spacing. It is anticipated that screws of the invention will be packaged and sold in sets including at least different compression member-to-head base dimensions.

The screw driver of the invention may comprise a simple open box socket at the distal end of a driver shaft axially aligned with a handle. The inside walls of the socket may be parallel and form a shape complementary to the outside dimensions of the screw head, with dimensions just sufficiently larger than those of the exterior of the head to enable the socket to slip easily over the head while maintaining a positive contact with the exterior faces of the head. A spacing one half percent to ten percent larger than the head width at its greatest width between parallel faces is suitable. The depth of the socket is preferably equal to the depth of the head ±10%. The exterior of the socket is smooth, and the wall thickness of the socket is as thin as is consistent with strength, to minimize the amount an incision must be spread to accommodate the driver. The exterior of the socket may be round to minimize interference with surrounding tissue as the driver is rotated, or the corners of a polygonal exterior may be rounded. The handle and socket may be formed as a single piece, or they may be separate pieces which are permanently or removably connected to each other. The socket and its shaft are preferably cannulated to accommodate cannulated screws. The socket and the shaft of the driver are preferably made of stainless steel, although titanium, titanium alloys, and other materials are useable.

Where the handle and socket are not removably connected, a kit of screwdrivers would consist of a screwdriver for each diameter of screw, illustratively a 2.0, 2.5, 3.0, 3.5, 4.0, 5.0, 6.0, and 7.0 mm size. Where they are removably connected, a single handle and appropriate sockets make up the kit. It will be understood that the shaft of the screwdriver could be made a part of the handle or a part of the removable socket, preferably of the socket.

In accordance with the method of the invention, a screw of the invention is inserted transfragmentally through a fracture, preferably at an angle to the fracture chosen for acceptably compressing the bone fragments in accordance with standard practice, and in order to place the head in an accessible position that will provide minimum patient discomfort. The screw is tightened into the distal bone fragment using the screwdriver of the invention, to place the compression member in contact with the proximal bone fragment and to draw the bone fragments into snug contact. Unlike many previously-known screws which are not specifically designed for removal, the screw of the present invention may, if desired, be driven through and beyond the margin of the distal bone fragment. This exit site is generally spaced far enough from the epidermis to prevent the production of a secondary wound. Screwing the internal fixation bone screw through the distal bone ensures that the screw is secured in cortical bone and is therefore less likely to lose purchase.

The tissue over the insertion site is then closed. When soft tissue closure over the screw involves capsule and/or subcutaneous layers, the capsule and layers can be closed over the screw head, a small incision made, and the layers pushed down below the head and over the compression member before closing the epidermis. On removal of the screw, only the epidermis needs to be incised to expose the screw head for removal of the screw. In most cases, further incision of the subcutaneous layers is not needed. This ease of removal is a major advantage of the present invention.

Previously, those concerned with internal fixation bone screws have believed that minimizing the protrusion of the head from the surface of the bone to which it is affixed is of great importance. See for example Zang, U.S. Pat. No. 5,556,225. In accordance with the present invention, accessibility of the head and ease of removing an internal fixation screw have been found to be more important. An additional advantage to having removable hardware that is easy to remove is that it is equally easy to replace. This means that should a screw lose purchase, a larger screw can serve as a replacement screw without the necessity of removal through a large incision and reevaluation of the exact size.

After the bone fracture has healed sufficiently, in accordance with radiographic and clinical evidence (frequently two to eight weeks after the procedure), the head of the screw is located either by palpation or by other means such as needle or fluoroscopy, and a small incision is made to expose the screw head.

Particularly if the screw head is near the surface, a small stab incision may be sufficient to access the screw head. The head of the screw may be cleaned, although this step is far less important than with a screw head relying on a depression in the top of the head for engagement with the driver. The screwdriver is placed over the head. Because the head is separate from the compression member, it is easily reached, and because the head is undercut, tilting the screwdriver allows it to exert a gentle outward force on the screw. The screwdriver is used for turning and removing the screw from the bone. The rounded shape of the head allows positive contact between the side walls of the driver socket and the head throughout a range of angles of at least fifteen degrees. Therefore, the driver may be tilted a few degrees from the axis of the screw, preferably around ten to twenty degrees, and used for gently lifting the screw.

When the screw is clear of the bone, it may be removed with forceps. The small incision is closed, preferably after bathing it. The bone is then allowed to regrow into the cavity left by the screw. It will be seen that the screw head will frequently be so close to the epidermis and will be so completely exposed by even a small incision, that removal of the screw may not even be dependent on the special qualities of the screwdriver.

The screw, driver, and methods of the present invention are particularly well suited to surgery on the human foot and hand. Examples are fractures of the phalanges, metatarsals, or talus of the foot, fractures of the phalanges or scaphoid of the hand, and in osteotomies of the hand and foot such as bunion repair through a modified Scarf/Akin osteotomy or a repair of a Jones fracture of the hand. It will be understood that osteotomies may involve both the removal of bone and the insertion of bone between bone fragments, so that the screw may pass through more than one proximal bone fragment. It will also be understood that the screw, driver, and methods of the invention are applicable to a wide range of other procedures on human and non-human vertebrate bones, including for example, other osteotomies and fractures of the hip, leg, arm, spine, or clavicle. The screw, driver and methods may also be useable with non-metallic, biocompatible, and bioabsorbable plating devices to avoid long-term exposure to metal components.

The foregoing and other objects, features, and advantages of the invention as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 1 is a view in perspective of one illustrative screw according to an embodiment of the present invention.

FIG. 2 is a view in side elevation of the screw of FIG. 1.

FIG. 3 is a top plan view of the screw of FIGS. 1 and 2.

FIG. 4 is a view in axial cross-section of the screw of FIGS. 2-3.

FIG. 5 is a detail in axial cross-section of a head part of the screw of FIGS. 2-4.

FIG. 6 is a detail view of a distal tip part of the screw of FIGS. 1-5.

FIG. 7 is a detail view in axial cross-section of a screw thread part of the screw of FIGS. 1-6.

FIG. 8 is a diagonal cross section taken along the line 8-8 of FIG. 3.

Corresponding reference numerals indicate corresponding parts throughout the several figures of the drawings.

DESCRIPTION OF THE PREFERRED EMBODIMENT

Figure 9:
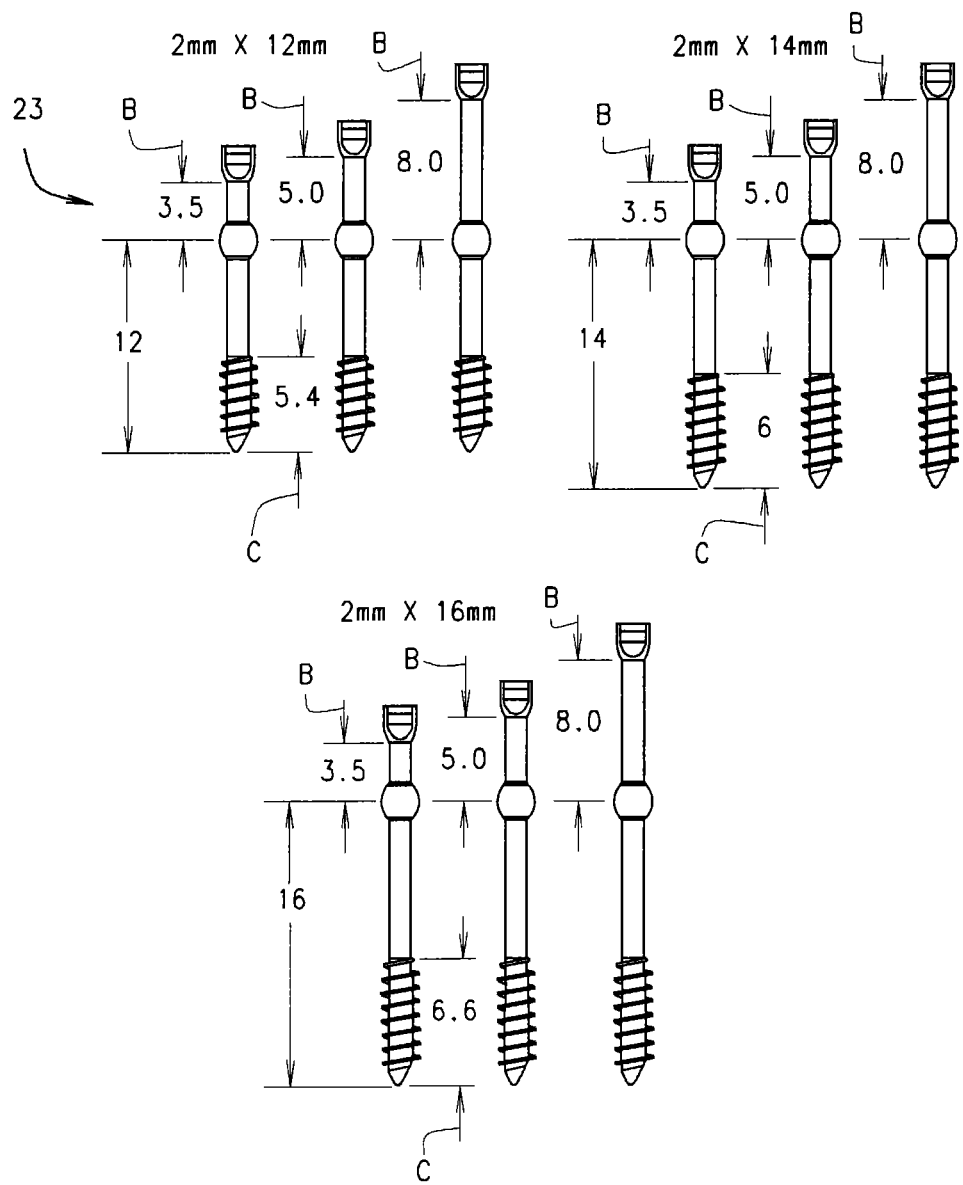
FIG. 9 shows a family of screws of the present invention, each screw having the same nominal length, but with different overall lengths determined by a head spacing dimension "B."

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

As shown in FIGS. 1-8, in accordance with one embodiment, a bone screw 1 comprises a thread 3 at its distal end, a head 5 at its proximal end, and a bone-engaging compression member 7 spaced distally from the head. The screw 1 may be made of any biocompatible material, but is preferably made of stainless steel, titanium, or titanium alloy. In this illustrative embodiment, it is made of the titanium alloy known as Ti6Al4V ELI, with an anodized finish in accordance with SAE AMS2488D.

The screw 1 is first identified by its diameter and by its length, as in a standard lag bone screw. Diameter is defined as the major diameter of the screw thread 3, in this illustrative embodiment 2.0 mm. The length A of the screw is measured from its distal end 9 to the largest diameter of the compression member 5. The size of the head 5 is nominally the same both across from face to face as it is tall (top to bottom), and both these dimensions are nominally the same as the screw diameter (major thread diameter). In this embodiment, the head is 2.0 mm across and 1.9 mm tall. Unique to the screw of the invention is a dimension B measured from the largest diameter of the compression member 5 to the base 11 of the head 5, as discussed more fully hereinafter. The minor diameter of the thread 3 is equal to the shaft diameter of the screw shaft 13 between the thread 3 and the compression member 7 and between the compression member 7 and the head base 11. That dimension in this embodiment is 0.75 times the major thread diameter, or 1.5 mm. The thread 9 has a length C that varies with the length of the screw 1. For a 16.0 mm long screw, the thread has a length of about 6 mm.

The thread 3 is self-tapping, but requires a pilot hole of about the diameter of the shaft 13.

The bone-engaging compression member 7 has a diameter from about 1.1 to about 1.25 times the diameter of the screw. In this illustrative embodiment, the compression member 7 is a sphere having a diameter of 2.2 mm.

The head 5 in this illustrative embodiment is generally in the form of a cube having a side nominally equal to the screw diameter. The top plan view (FIG. 3) of the head 5 shows the sides as straight, but as viewed in side elevation (FIG. 2) or in cross-section (FIGS. 4 and 5), the sides are sloped inward top and bottom at an angle of 16° from a maximum convex dimension 15, as indicated at 17 and 19 respectively.

The spacing distance B between the base 11 of the head 15 and the widest part of the compression member may be chosen to suit the use of the screw. In this illustrative embodiment, as shown in FIG. 9, a set 23 of "long head" screws have spacing distance B of 3.5 mm, 5.0 mm, and 8.0 mm, respectively. For applications in which little room is available below the skin, a "short head" having a spacing distance of 1.0 mm, is provided.

The head 5 and compression member 7 are formed to be smooth, with no sharp edges.

The illustrative screw is cannulated, having a central bore 21 of 0.75 (+0.05) mm.

A solid screw would look the same, but without the central cannula.

Figure 10:
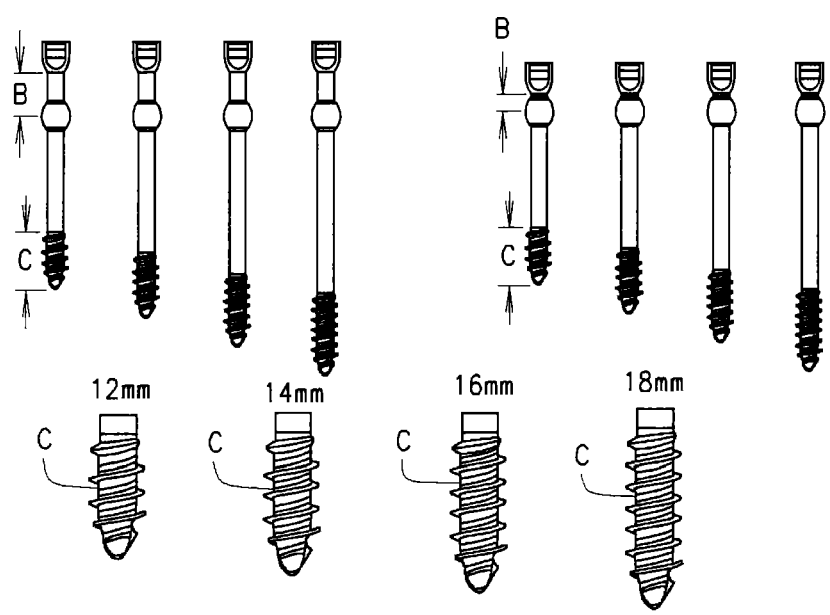
FIG. 10 shows a family of screws of the present invention, one group of screws having a "long" head spacing dimension "B" and a second group having a short head spacing dimension "B", each screw in each group having different nominal lengths and different thread lengths "C".
Figure 11:
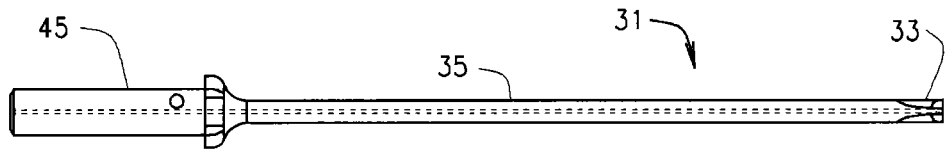
FIG. 11 is a view in side elevation of a screw driver according to an embodiment of the present invention.
Figure 12:
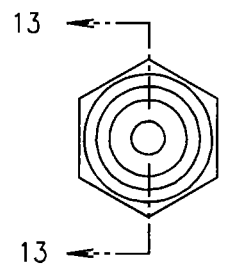
FIG. 12 is an end view of the driver of FIG. 11.
Figure 13:
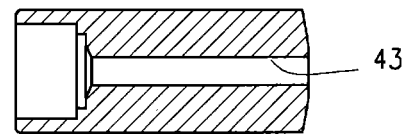
FIG. 13 is a fragmentary axial cross-section of a socket portion of the driver of FIGS. 11 and 12, taken along the line 13-13 of FIG. 12.
Figure 14:
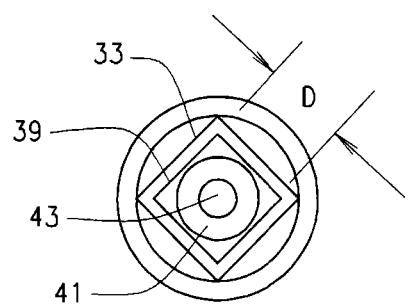
FIG. 14 is an end view of the fragment of FIG. 13.
Figure 15:
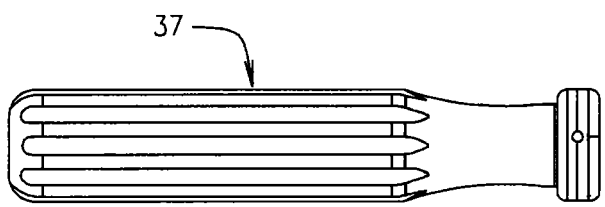
FIG. 15 is a view in side elevation of a handle part of the driver.
Figure 16:
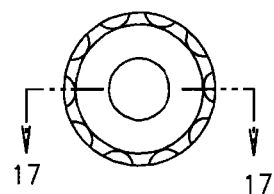
FIG. 16 is an end view of the handle of FIG. 15.
Figure 17:
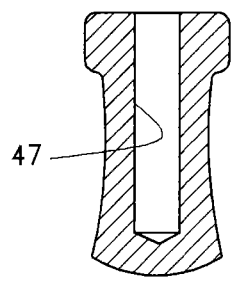
FIG. 17 is a fragmentary sectional view taken along line 17-17 of FIG. 16.

As indicated in FIG. 10, each family includes screws of different lengths, measured from the distal end of the screw to the maximum diameter of the compression member, ranging from 12 mm to 60 mm in two millimeter increments. Each length of each family in turn includes different compression member-to-head base dimensions "B": 1.0 mm ("short head"), 3.5 mm, five millimeters, and eight millimeters. Because the size of the screw head in each family is constant, the overall length of the screws of a given nominal length vary based on the length of the compression member to head spacing. As shown in FIG. 10, different lengths of screw 1 will have different thread lengths "C".

An illustrative screw driver 31 of the invention is shown in FIGS. 11-17. The driver 31 comprises a simple open box socket 33 formed integrally at the distal end of a driver shaft 35 axially aligned with a handle 37, as shown in FIGS. 11-17. The shaft 35 and socket 33 have an overall length of about 125 mm. The shaft and socket are formed from a single 0.375 mm diameter rod of 17-4PH H900 stainless steel and passivated per ASTM A967. At its distal end, the round tube is squared and routered to form inside walls 39 of the socket. The inside surfaces of the walls 39 are flat and parallel and have a side "D" of 2.07 +/−0.01, just larger than the sides of the screw head 5. The depth of the socket is 2.0 mm, about 0.1 mm deeper than the height of the screw head. A shallow well 41 at the bottom of the socket 33 acts as a guide for a K-wire to enter a 0.90 +/−0.05 mm cannula 43 extending through the driver shaft 35. The exterior of the socket 33 is smooth, and the wall thickness of the socket is as thin as is consistent with strength, to minimize the amount an incision must be spread.

The shaft 35 of the driver 31 has welded to its proximal end a standard adapter 45 sized to fit a hollow 47 in the handle 37, to which it is attached. The handle 37 is formed of polyphenylsulfone (Radel® R5500, Solvay Advanced Polymers L.L.C). In this embodiment, the handle 37, shaft 35, and socket 33 are packaged as a single unit, with handles of different colors signifying different socket sizes.

A kit of screwdrivers in this embodiment consists of eight screwdrivers, each with a handle 37 secured to a shaft/socket of an appropriate size for each diameter of screw, in this illustrative embodiment a 2.0, 2.5, 3.0, 3.5, 4.0, 5.0, 6.0, and 7.0 mm size.

An example of the use of the screw, driver, and method of the present invention to treat a bunion using the Akin procedure was conducted as follows:

A chevron style osteotomy was made through and into the head of the first metatarsal.

Next, a 0.062 Kirschner wire was utilized to drill a pilot hole through both sides of the osteotomy.

Next, a depth gauge was utilized to determine the appropriate screw length.

Next a countersink was performed at the proximal entry point of the k-wire.

Next, an appropriately sized bone screw was screwed into the osteotomy and compression was noted and achieved to two finger tightness.

Next capsular closure was performed over the head of the screw creating a mild tenting effect directly over this.

Upon the completion of capsular closure the screw head was palpated and a small stab incision was made into the capsule whereby the head of the screw was pushed through the capsule exposing the head.

Next the sub-cuticular layer was closed once again over the head of the screw creating a mild tenting.

Upon the completion of the sub-cuticular closure the screw head was again palpated and a small stab incision was made to expose the screw head through this layer.

Finally, the epidermal layer was closed utilizing absorbable 5-0 Vicryl suture. On completion of this closure it is noted that there is no tenting of the epidermis due to screw head prominence. Palpation of the screw head can, however, be appreciated through the epidermis.

After an appropriate period, removal was conducted as follows:

The patient was brought into the operating room and prepped and draped in the usual aseptic manner.

Next, attention was directed to the dorsal aspect of the foot which was palpated locating the head of the previously applied cortical removable bone screw.

Next, approximately 1.5 mL of lidocaine one percent was utilized to achieve anesthesia.

Next, a stab incision was made with a number eleven blade directly over the head of the previously mentioned screw.

Next, the driver was placed into the wound and the screw head was located and securely contact fitted around the driver head. The driver was tilted at approximately 15° to create the appropriate pulling effect as the screw was removed. Once the screw head was noted to exit the small epidermal incision, a small hemostat was utilized to secure the skin around the screw head and allow further secure removal of the screw.

Upon complete removal, the remaining incision was closed with a single 5.0 nylon suture.

Another example of the use of the present invention is shown schematically in

Figure 18:
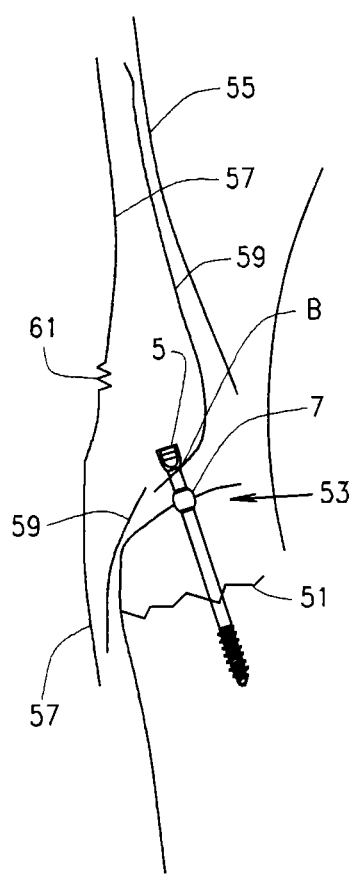
FIGS. 18 and 19 are schematic views of the fixation of a fracture with the screw 1 and driver 31 of the invention.
Figure 19:
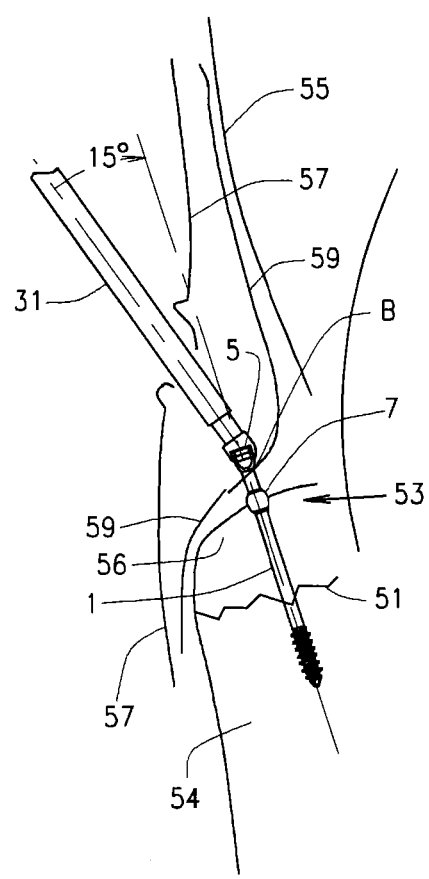

FIGS. 18 and 19. An incision is made through the epidermis 57 and subdermal tissue 59, and they are retracted. The fracture in bone 53 is reduced by manipulation, and drilled with a K-wire through both a proximal fragment 56 and a distal fragment 54 at an angle to the fracture chosen for acceptably compressing the bone fragments in accordance with standard practice, and in order to place the head in an accessible position that will provide minimum patient discomfort. The K-wire is removed, and the bone fragment 56 is mildly countersunk. The depth of the hole is measured with a depth gauge. A proper size cannulated screw 1 is chosen based on angle of entry and concavity of bone surface and distance from bone surface to skin surface. A K-wire having both ends tapered is inserted, and the screw 1 is tightened over it to two finger tightness and good compression using the screwdriver 31. The K-wire is removed. The capsule 59 is closed over the head 5, tenting the capsule. The capsule is then incised directly over the screw head 5 to expose the head. Any subcutaneous tissue is likewise closed over the head 5, incised to expose the head, and closed. The epidermis 57 is then closed and sutured as indicated at 61.

The screw 1 is removed in the same way as in the previous example, requiring only a small stab incision to expose the screw head 5 and allow removal of the screw.

Numerous variations, within the scope of the appended claims will occur to those skilled in the art in light of the foregoing description. Merely by way of example, although standard thread count and spacing will typically be used, the thread count, spacing, or both may be changed from screw to screw, without departing from the scope of the present invention. The shape of the head and its spacing from the compression member may be varied widely.

Figure 20:
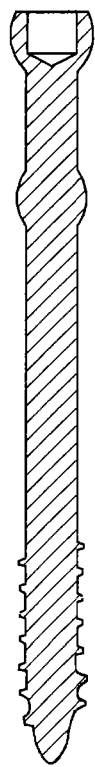
FIG. 20 is a cross-sectional view corresponding to FIG. 4 of another embodiment of bone screw.

The head may even be made with a conventional hex socket and driven with a conventional hex-head driver as shown in FIG. 20, corresponding to FIG. 4. This approach allows a slightly more rounded head, but it suffers from the problems of ingrowth into the hex socket and possible difficulties in removing the screw. Leaving a neck below the head and above the compression member, however, is highly advantageous in providing purchase for aiding in the extraction of the screw. The slight angulation of the driver allows for the retrograde force frequently needed to remove the screw.

Figure 21:
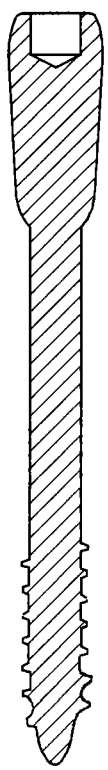
FIG. 21 is a cross-sectional view corresponding to FIGS. 4 and 19 of yet another embodiment of bone screw.

As shown in FIG. 21, it is even possible to obtain some of the advantages of the present invention by melding the compression ball and the head of the embodiment of FIGS. 1-8 into a single body. That approach does elevate the head to a more reachable position, but it is believed to lack most of the other advantages of the illustrative embodiments.

Screw head shape can be square, triangular, rectangular, oblong, or any other shape that will facilitate this process. It is believed at present that having at least two convex opposed faces is advantageous for positive driving of the screw in both directions and for lifting the screw as it is removed. The shape of the compression member may also be varied. A ball shape, whether spherical or flattened, is preferred because of its lack of edges, and because it distributes stresses efficiently. The size of the compression member may be varied; it is believed that a somewhat larger ball, perhaps one millimeter larger than presently preferred, may give somewhat improved results.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

All of the patents, patent applications, and literature references mentioned herein are hereby incorporated by reference.

The invention claimed is:

1. A bone screw made of a biocompatible material, the bone screw being sized and shaped to fix bone fragments of an osteotomy or fracture of a bone and to be removed after bone healing has progressed, the bone screw comprising:
   a thread at a distal end of the screw, the thread having a major diameter and a minor diameter;
   a head at a proximal end of the screw;
   a bone-engaging compression member spaced distally from the head, the bone-engaging compression member being convex on a distal side, convex on a proximal side, and circular in cross-section, and having a smoothly curved outline without edges to permit easy extraction through an incision, the compression member having a maximum diameter from 10% to 70% greater than the major diameter of the thread; and
   a neck extending from the head to the compression member, the neck being of smaller diameter than the major diameter of the thread throughout its length,
   the head and the neck being free of sharp edges;
   wherein the compression member is a ball having a maximum diameter, and wherein the maximum thread diameter is two to seven millimeters, a distance (A) between a distal end of the screw and the maximum diameter of the ball is twelve to sixty millimeters, and a distance (B) between a distal end of the head and the maximum diameter of the ball is one to nine millimeters.

2. The bone screw of claim 1 wherein the enlarged compression member is generally spherical.

3. The bone screw of claim 1 wherein the head is non-circular.

4. The bone screw of claim 3, wherein the head in plan view is generally a regular polygon.

5. The bone screw of claim 4 wherein the polygon has an even number of sides.

6. The bone screw of claim 5 wherein at least two opposing sides of the polygon are convex.

7. The bone screw of claim 1 wherein the screw is cannulated.

8. The bone screw of claim 1 wherein a section of the screw extending from the compression ball to the screw thread has a uniform diameter, the diameter of the section and the diameter of the neck being generally equal to the minor diameter of the screw thread.

9. The bone screw of claim 1 wherein the head is a regular polygon having an even number of sides and rounded edges, a distance between opposed sides of the head being about equal to the major diameter of the screw thread.

10. The bone screw of claim 9 wherein the distance between opposed sides of the head is equal to the major thread diameter ±5%, the sides of the head being arcuate from a distal end to a proximal end of the head, a proximal surface of the head being smooth.

11. A set of bone screws, the set comprising at least two screws each in accordance with the bone screw of claim 1 and having the same distance (A) between the distal end of the screw and the maximum diameter of the ball and having different distances (B). between the distal end of the head and the maximum diameter of the ball.

12. A bone screw made of a biocompatible material, the bone screw being sized and shaped to fix bone fragments of an osteotomy or fracture of a bone and to be removed after bone healing has progressed, the bone screw having a long axis, a distal end and a proximal end, the bone screw comprising:
   a screw thread at the distal end of the screw, the thread having a major thread diameter of from two to seven millimeters, a minor thread diameter, and an axial length (C);
   a head at the proximal end of the screw, the head having a proximal end and a distal end, the distal end being convex, the head being a square or a regular hexagon in axial view, a distance between opposed sides of the square or hexagon being about equal to the major thread diameter ±5%, the proximal end and the distal end of the head being spaced apart a distance on the order of 80% to 100% of the distance between opposed sides of the square or hexagon, the head being free of sharp edges;
   a bone-engaging compression ball spaced distally from the head, the bone-engaging compression ball having a smoothly curved outline without edges to permit easy extraction through an incision, the compression member having a maximum diameter in a plane perpendicular to the long axis of the screw from 10% to 70% greater than the major diameter of the thread, a distance (A) from the distal end of the screw to the maximum diameter of the compression ball being from twelve to sixty millimeters and being more than about twice the axial length (C) of the screw thread; and
   a neck extending from the head to the compression member, a distance (B) from the distal end of the head to the maximum diameter of the compression ball being from one to nine millimeters;
   the neck and a section of the screw between the compression ball and the screw thread both having a uniform diameter about equal to the minor thread diameter.

* * * * *